(12) United States Patent
Couladouros et al.

(10) Patent No.: US 7,038,067 B2
(45) Date of Patent: May 2, 2006

(54) PROCESS FOR SYNTHESIZING D-TOCOTRIENOLS FROM 2-VINYLCHROMANE COMPOUND

(75) Inventors: Elias A. Couladouros, Athens (GR); Andreas M. Papas, Kingsport, TN (US); Vassilios I. Moutsos, Athens (GR); Maria Lampropoulou, Athens (GR)

(73) Assignee: Yasoo Health, Inc., Johnson City, TN (US)

( * ) Notice: Subject to any disclaimer, the term of this patent is extended or adjusted under 35 U.S.C. 154(b) by 0 days.

(21) Appl. No.: 10/962,390

(22) Filed: Oct. 12, 2004

(65) Prior Publication Data

US 2005/0124688 A1    Jun. 9, 2005

Related U.S. Application Data

(60) Provisional application No. 60/510,196, filed on Oct. 10, 2003.

(51) Int. Cl.
*C07D 311/04*    (2006.01)

(52) U.S. Cl. .................................................... 549/398
(58) Field of Classification Search ................. 549/398
See application file for complete search history.

(56) References Cited

U.S. PATENT DOCUMENTS

| 5,190,618 | A | 3/1993 | Top et al. |
| 5,495,026 | A | 2/1996 | Fukumoto |

FOREIGN PATENT DOCUMENTS

| JP | 63063674 A2 | 9/1986 |
| JP | 01233278 A2 | 3/1988 |
| JP | 200302777 | 4/1999 |
| JP | 2003171376 | 6/2000 |

OTHER PUBLICATIONS

Chenevert et. al., "Synthesis of (S)-alpha-tocotrienol via an enzymatic desymmetrization of an achiral chroman derivative", Tetrahedron Letters, vol. 43, Issue 44, Oct. 28, 2002, pp. 7971-7973.*
Machlin, "Vitamin E: A Comprehensive Treatise", (1980) 7-65, Dekker, New York.
Pappas, ed. "Antioxidant Status, Diet, Nutrition, and Health", (1999) 479-496, CRC Press, USA.
Chenevert & Courchesne, *Tetrahedron Letters*, 43 (2002) 7971-7973.
Pearce et al, *J. Med. Chem.* 35 (1992) 3595-3606.
Karrer & Rentschler, *Helv. Chim. Acta.* 27 (1944) 1297-1300.
McHale et al., *J. Chem. Soc.* (1963) 784-791.
Schudel et al., *Helv. Chim. Acta.* 46 (1963) 2517-2526.
Mayer et al., *Helv. Chim. Acta.* 50 (1967) 1376-1393.
Kabbe & Heitzer, *Synthesis* (1978) 888-889.
Kajiwara et al., *Heterocycles* 14 (1980) 1995-1998.
Urano et al., *Chem. Pharm. Bull.* 31 (1983) 4341-4345.
Pearce et al., *J. Med. Chem.* 35 (1992) 3595-3606.
Pearce et al., *J. Med. Chem.* 37 (1994) 526-541.
Scott et al., *Helv. Chim. Acta.* 59 (1976) 290-306.
Greene & Wuts, "Protecting Groups in Organic Synthesis", 3rd ed., Wiley, New York (1999) 249-287.
Eren & Keinan, *J. Am. Chem. Soc.* 110 (1988) 4356-4362.
Hyatt & Skelton, *Tetrahedron: Asymmetry*, 8 (1997) 523-526.
March, "Advanced Organic Chemistry", 4th ed., Wiley, New York (1992) 1177-1182.

(Continued)

*Primary Examiner*—Cecilia J. Tsang
*Assistant Examiner*—Binta Robinson
(74) *Attorney, Agent, or Firm*—Donna J. Russell

(57) ABSTRACT

A process of forming a d-tocotrienol from a (2S)-vinylchromane compound, through hydroboration of the (2S)-vinylchromane to provide an organoborane, followed by coupling the organoborane with a halogenated C-14 sidechain compound under conditions of palladium-catalyzed cross-coupling is taught. Methods for providing the (2S)-vinylchromane compound and the halogenated C-14 compound are disclosed.

15 Claims, No Drawings

OTHER PUBLICATIONS

Hegedus, "Transition Metals in the Synthesis of Complex Organic Molecules", Universiyt Science Books, Mill Valley, Calif. (1994) 261-303.
Miyaura & Suzuki, *Chem. Rev.*, (1995) 2457-2483.
Ismail et al., *Tetrahedron Letters*, 33 (1992) 3795-3796.
Hudlicky, "Oxidations in Organic Chemistry", ACS, Washington, D.C. (1990) 114-126.
Trost et al., *J. Am. Chem. Soc.*, 126 (2004) 11966-11983.
Sakito & Suzukamo, *Tetrahedron Letters*, 23 (1982) 4953-4954.
Solladie & Moine, *J. Am. Chem. Soc.* 106 (1984) 6097-6098.
Bouzbouz et al., *Euro. J. Org. Chem.*, 18 (2000) 3223-3228.
Hubscher & Barner, *Helv. Chim. Acta.*, 73 (1990) 1068-1086.
Barner & Schmid, *Helv. Chim. Acta.*, 62 (1979) 2384-2399.
Wolff et al., *Tetrahedron Letters*, 43 (2002) 2555-2559.
Cohen et al., *J. Org. Chem.*, 46 (1981) 2445-2450.
Mayer et al., *Helv. Chim. Acta.*, 46 (1963) 650-671.

* cited by examiner

PROCESS FOR SYNTHESIZING D-TOCOTRIENOLS FROM 2-VINYLCHROMANE COMPOUND

CROSS REFERENCES TO RELATED APPLICATIONS

This application claims the benefit of U.S. Provisional Application Ser. No. 60/510,196 filed Oct. 10, 2003.

FIELD OF THE INVENTION

This invention relates generally to processes for producing certain compounds in the Vitamin E family, also known generally as tocols. In particular, the invention relates to processes for producing tocotrienols having the structure and absolute configuration the same as found in nature.

BACKGROUND OF THE INVENTION

There are four naturally occurring tocotrienols, d-alpha-, d-beta-, d-gamma-, and d-delta-tocotrienol. The four naturally occurring tocotrienols have the (R) absolute configuration at the C-2 chroman ring position, and the chemical structures wherein $R_1$ (at C-5 chroman ring position), $R_2$ (at C-7 chroman ring position), and $R_3$ (at C-8 chroman ring position) are methyl in the d-alpha- homologue, $R_1$ and $R_3$ are methyl in the d-beta-homologue, $R_2$ and $R_3$ are methyl in the d-gamma- homologue, and $R_3$ is methyl in the d-delta homologue, with the non-methyl R groups being hydrogen atoms.

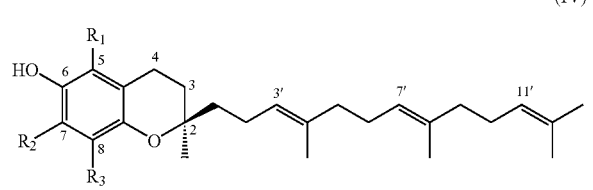

(IV)

The chroman ring numbering system referenced above is used herein for continuity. As shown, each of the four naturally occurring d-tocotrienols has an (R) absolute configuration at the chiral 2-position carbon of the chroman ring. Further, the tocotrienols have a trans double bond site at each of the 3' and 7' chain positions in the 16-carbon side chain attached to the chroman ring. The geometry of each of these double bond sites is trans (also referred to as E) in all four natural tocotrienols.

For a general discussion of the natural tocotrienols, see L. Machlin, ed., "Vitamin E: A Comprehensive Treatise", Dekker, N.Y., 1980, pp. 8–65.

The family of d-tocotrienols has been shown to possess a wide variety of health benefits. For a discussion of the health-promoting benefits of tocotrienols, see T. R. Watkins, et al., "Tocotrienols: Biological and Health Effects", K. L. Jordan Heart Foundation, Montclair, N.J., 1999; C. Chenevert and G. Courchesne, "Synthesis of (S)-alpha-Tocotrienol via an enzymatic desymmetrization of an achiral chroman derivative", Tetrahedron Letters 43, 7971–7973 (2002); and B. C. Pearce et al., "Hypocholesterolemic Activity of Synthetic and Natural Tocotrienols", J. Med. Chem. 35, 3595–3606 (1992).

d-Tocotrienols are present in the oils, seeds, and other parts of many plants used as foods (see pp. 99–165 in L. Machlin, ed., "Vitamin E: A Comprehensive Treatise" for a discussion of the occurrence of tocotrienols in foods). However, since d-tocotrienol levels are very low in these natural sources it is often necessary to supplement the typical human diet with additional tocotrienols in order to realize the potential health advantages provided by these compounds. Tocotrienol-containing concentrates can be prepared from certain plant oils and plant oil by-products such as rice bran oil or palm oil deodorizer distillate. For examples of such isolation processes, see for instance A. G. Top et al., U.S. Pat. No. 5,190,618 (1993) or Y. Tanaka and T. Ichitani, Jpn. Kokai Tokkyo Koho appl. JP 2002-168227 20020610 (2003), CAN 139:52035.

There are two problems inherent in obtaining d-tocotrienols from natural sources. Firstly, there is only a limited and inadequate supply of the requisite plant or seed oils available for use as tocotrienol feedstocks. Secondly, the d-tocotrienol yield from such processes is a mixture of varying amounts of all of the natural tocols. In order to obtain a pure member of the d-tocotrienol family, it has been necessary to resort to very expensive procedures such as preparative scale reversed-phase chromatography or simulated moving bed chromatography. For an example of such a purification process, see M. Kitano et al., Japanese Patent No. 200302777 (2003), CAN 133:309299.

In view of the limited availability and difficulty of isolation of natural d-tocotrienols, it is necessary to seek ways for obtaining the materials through chemical synthesis from commercially available raw materials. The synthesis of tocotrienols in the natural d- form, having the (2R) chiral configuration and trans double bonding at the proper locations in the side chain, has heretofore proven to be of considerable difficulty.

The first attempt to synthesize a member of the tocotrienol family was reported by P. Karrer and H. Rentschler (Helv. Chim. Acta 27, 1297–1300 (1944)); these workers failed to synthesize tocotrienols. Karrer and Rentschler obtained compounds having cyclization of the side chain. A later attempt by D. McHale et al. (J. Chem. Soc. 1963, 784–791) likewise failed due to inadvertent cyclization of the olefin-containing side chain.

Syntheses of various members of the tocotrienol family in the d,l- or (RS)-form have been published. Schudel et al. (Helv. Chim. Acta 46, 2517–2526 (1963)) completed a synthesis of alpha- and delta-tocotrienols in racemic form (dl-alpha- and delta-tocotrienols, each having a 50/50 mixture of R- and S-enantiomers at the 2-position). Schudel's synthesis was not amenable to synthesis of the natural 2R-isomer. Other tocotrienol syntheses include the works reported by H. Mayer et al., Helv. Chim. Acta 50, 1376–11393 (1967); H.-J. Kabbe and H. Heitzer, Synthesis 1978, 888–889; M. Kajiwara et al., Heterocycles 14, 1995–1998 (1980); S. Urano et al., Chem. Pharm. Bull. 31, 4341–4345 (1983), Pearce et al., J. Med Chem. 35, 3595–3606 (1992), and Pearce et al., J. Med. Chem. 37, 526–541 (1994). As in the case of Schudel et al., none of these reported processes lead to the natural d-form of the tocotrienols, but rather produces racemic mixtures.

Several syntheses of natural form d-tocotrienols have been published. J. Scott et al., Helv. Chim. Acta 59, 290–306 (1976), started with trimethyl-hydroquinone and used a conventional optical resolution to provide the key intermediate 2,5,7,8-tetramethyl-6-hydroxychroman-2-acetic acid in the natural enantiomeric form. This compound was then elaborated into d-alpha-tocotrienol by a thrice-iterated process of adding 5-carbon sections of the side chain at a time, as follows:

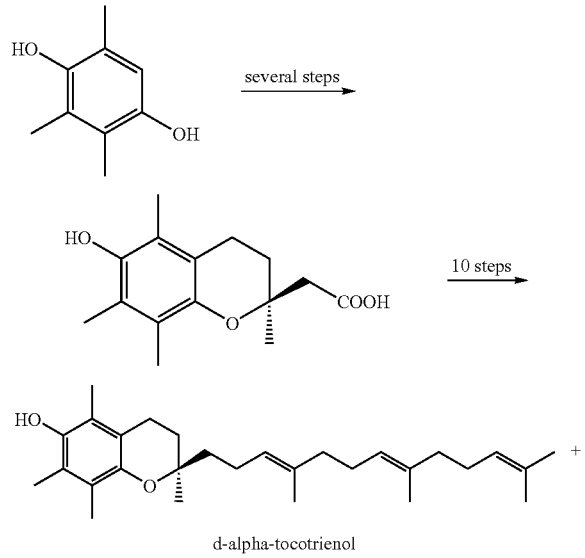

d-alpha-tocotrienol

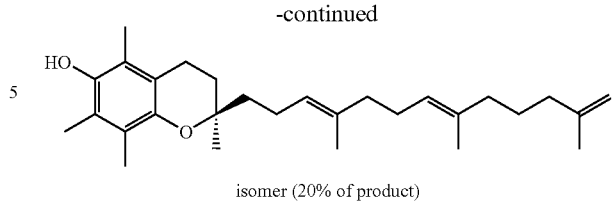

isomer (20% of product)

Unfortunately this synthesis produced d-alpha-tocotrienol contaminated with about 20% of the isomeric compound shown. The authors were unable to separate pure natural-form tocotrienol from this mixture.

Sato et al. (Japanese Patent 63063674 A2 19880322 Showa; CAN 110:193145) described an approach to d-alpha-tocotrienol in which the diterpene alcohol geranylgeraniol is converted to an epoxytriene through Sharpless asymmetric epoxidation. The epoxidation is elaborated through several steps into the chiral acetoxy sulfide shown below. This $C_{20}$ chain is then attached to a suitably protected trimethylhydroquinone to provide the illustrated open-chain sulfide. The sulfide was subsequently desulfurized, the acetates removed, and cyclized to form a chiral chroman, as shown:

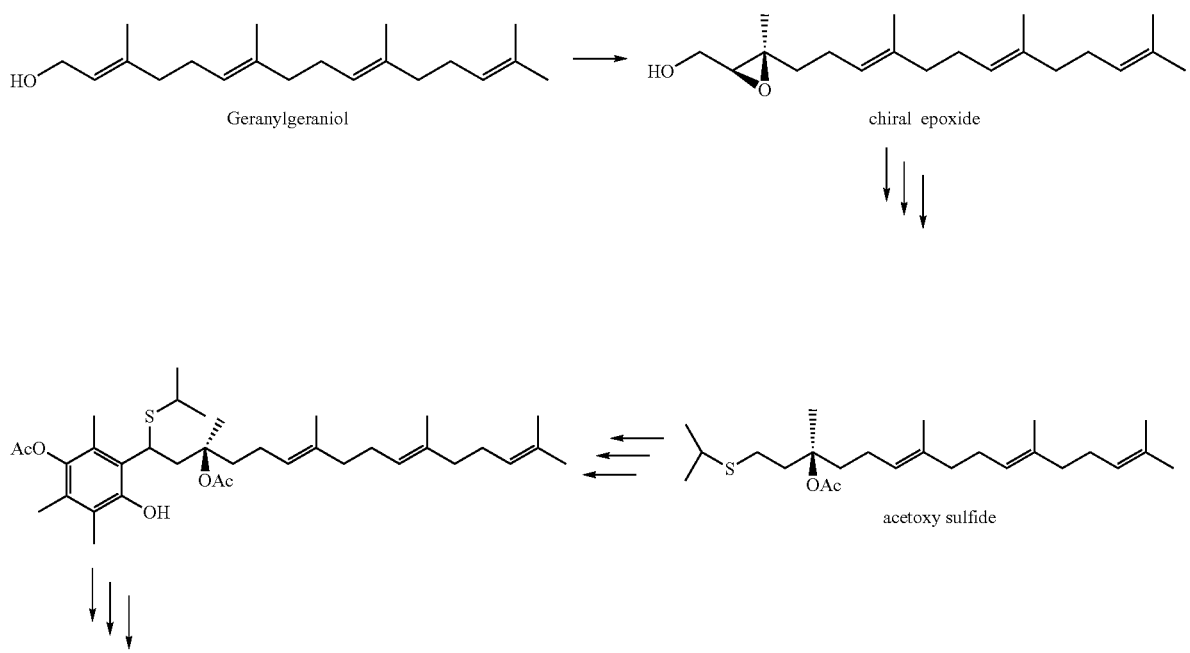

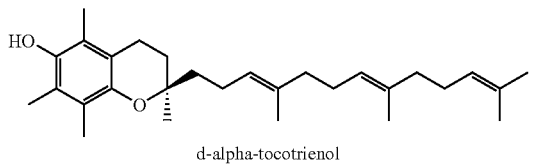

d-alpha-tocotrienol

While the above synthesis produces natural-equivalent d-alpha-tocotrienol, it suffers from the fact that the geranylgeraniol starting material is very difficult to obtain.

In an apparent effort to overcome this difficulty, Sato et al. (JP 01233278 A2 19890919 Heisei, 1989; CAN 112:139621) report a second synthesis of d-alpha-tocotrienol which replaces the use of geranylgeraniol with a much more readily available side-chain synthon, the p-tolylsulfone derived from the readily available $C_{10}$ terpene alcohol, geraniol. This synthesis, outlined below, requires an unsuitably large number of steps for commercial use.

the chiral 2-position carbon. Unnatural (S) or (l)-alpha-tocotrienol was thereafter produced from the 14-carbon (R)-chromanol compound via substituting the hydroxyl group at the 6-position with a benzyl ester protecting group, substituting the hydroxyl portion of the 2-hydroxymethyl group with a triflate (—$OSO_2CF_3$) leaving group to form a triflated chroman protected at the 6-position. The triflated chroman was thereafter coupled with phenyl farnesyl sulfone, i.e., a 15-carbon branched carbon chain having three methylated trans double bond sites corresponding to the 16-carbon side chain of a tocopherol, less the methyl carbon

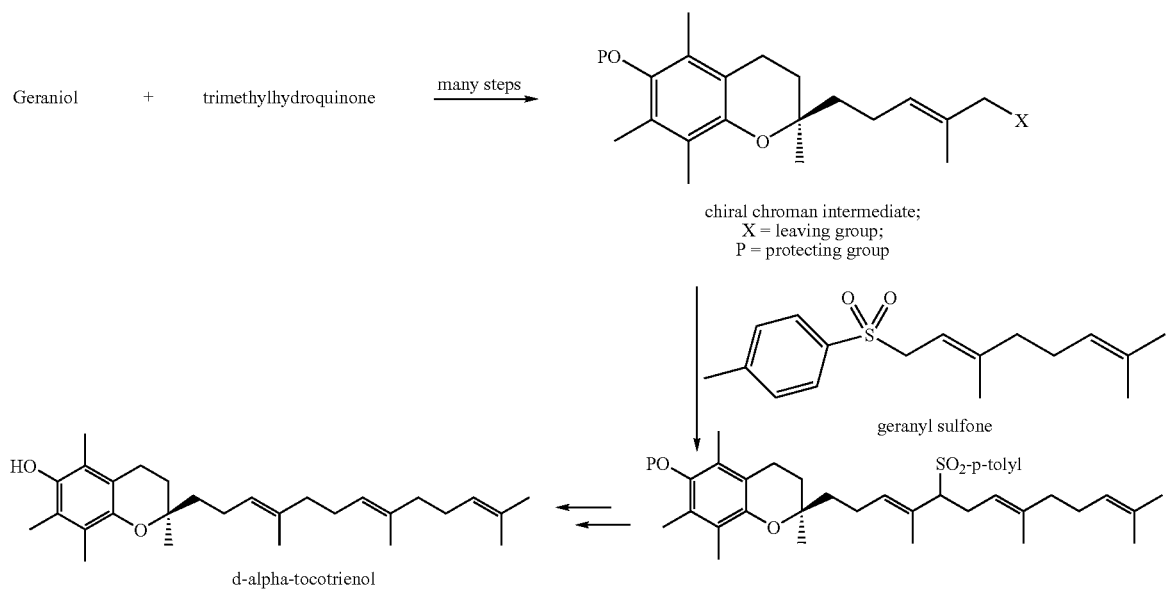

In other relevant syntheses, Scott et al. prepared a chiral $C_{15}$ chroman and added 5-carbon chains to it three times to make the final product tocotrienol. Sato used a $C_9$ hydroquinone and a $C_{20}$ chain derived from geranylgeraniol. Sato used an intermediate $C_{18}$ chroman section and a $C_{10}$ geranyl section.

In the only reported synthesis in the tocotrienol area that is truly highly convergent, Chenevert and Courchesne (*Tetrahedron Letters* 43, 7971–7973 (2002)) formed unnatural (S) or (l)-alpha-tocotrienol in a process starting with the achiral triol, dl-chromantriol. As shown in the process illustrated below, Chenevert and Courchesne first converted the achiral triol to a (S) monoester via enzymatic desymmetrization and acetylation. Then, the (S) monoester was further treated with two equivalents of mesyl chloride to provide a (R) dimesylated monoester chroman. Reduction of the dimesylated monoester chroman produced (R)-chromanol, a chroman substituted with a hydroxymethyl group at the 2-position and a hydroxyl group at the 6-position of the chroman ring, and having (R) absolute configuration at attached to the 2-position carbon of the chroman ring. As generation of the carbanion from the sulfone allowed for farnesyl group alkyl substitution of the triflate leaving group on the chroman ring, alpha-tocotrienol retaining the unnatural (S) or (l) configuration at the chiral chroman carbon is produced. The process is illustrated below:

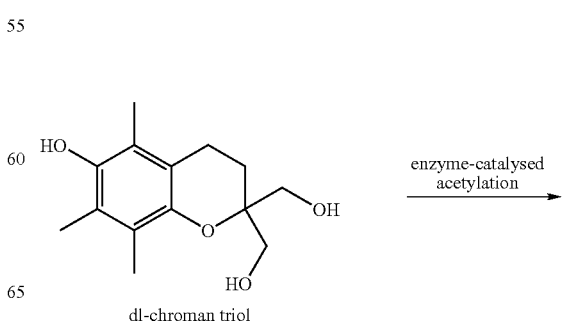

dl-chroman triol

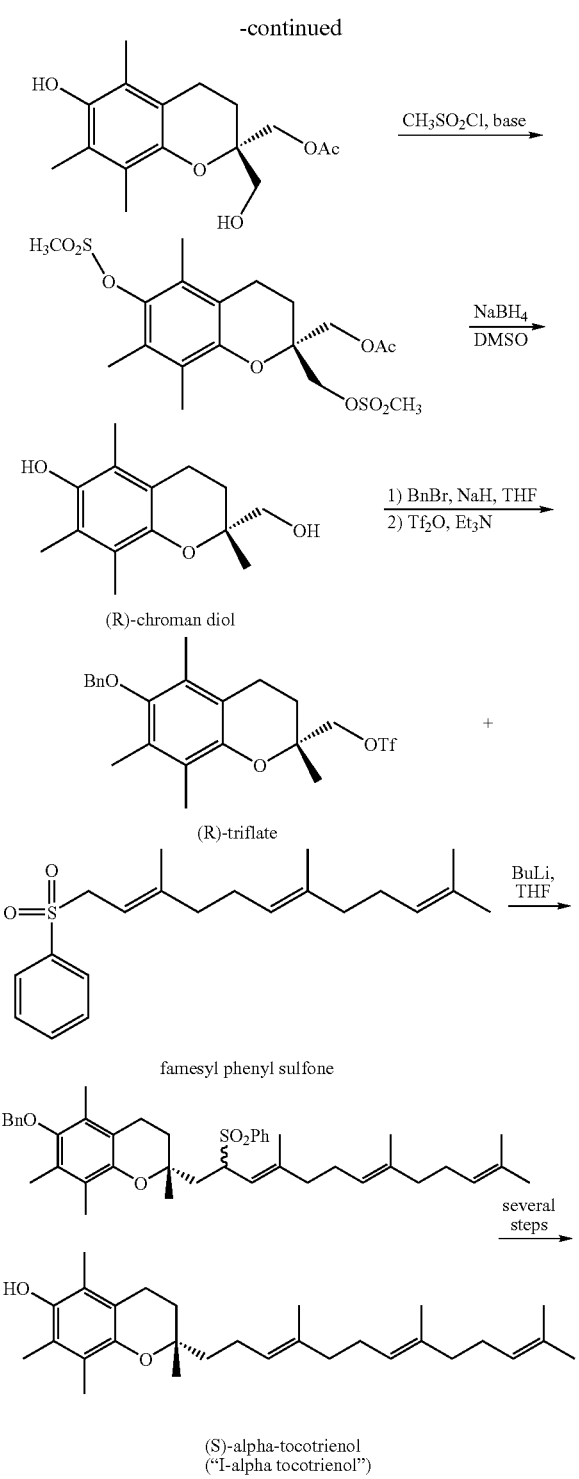

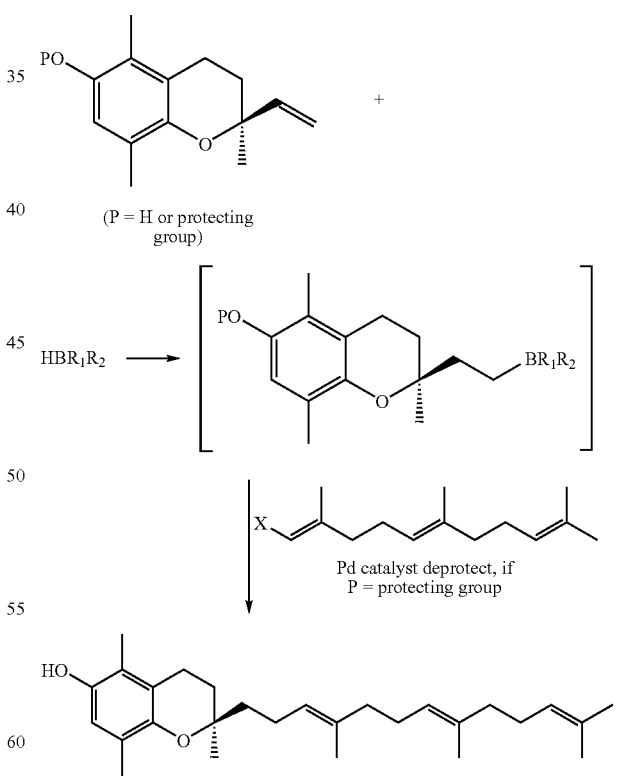

The use of the achiral chroman triol as starting material in the (l)-alpha-tocotrienol synthesis of Chenevert and Courchesne does not show any advantages in either yield, number of steps, or economic advantage over previously reported chemistry that has suffered from being unattractive in each of these aspects. Moreover, the tocotrienol produced thereby is in the unnatural, and far less useful, (l) enantiomeric form.

In light of the above, there remains a need for commercially suitable processes of synthesizing members of the naturally occurring d-tocotrienol family using commercially available starting materials and requiring a number of steps that is economically feasible on a commercial scale. New routes for producing heretofore relatively unavailable starting materials for such synthesis would be valuable. In particular, there is a need for a more economically acceptable starting materials and syntheses for making each of d-beta, d-gamma, and d-delta tocotrienols.

BRIEF SUMMARY OF THE INVENTION

In accordance with the purposes of this invention, as embodied and broadly explained herein, this invention, in one aspect, relates to a novel process for preparing d-beta-, d-gamma-, and d-delta-tocotrienols in which a suitably prepared 2-vinylchroman of substantially single enantiomer composition is converted, through hydroboration, to an unisolated organoborane intermediate which is then coupled, under the conditions of palladium-catalysed cross-coupling (Suzuki reaction), with 1-bromo- or 1-iodo-2,6,10-trirethylundeca-1E,5E,9-triene. This process can be represented in schematic form by the following chemical equations (illustrated for the case of d-beta-tocotrienol only, but the invention applies equally to the gamma- and delta-isomer and homolog):

In another aspect of this invention, the invention relates to a method of providing the requisite single-enantiomer 2-vinylchroman compound through Wittig olefination of the corresponding single enantiomer aldehyde:

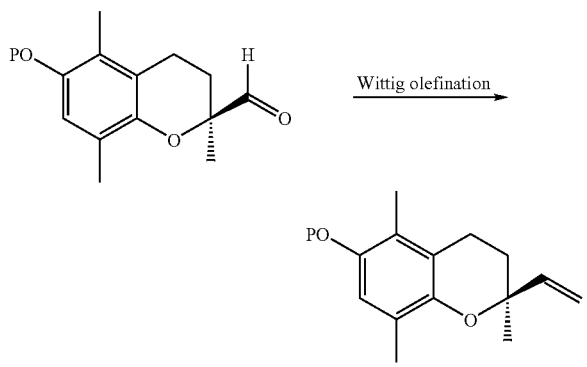

This aldehyde is readily available through oxidation of the corresponding single-enantiomer alcohol:

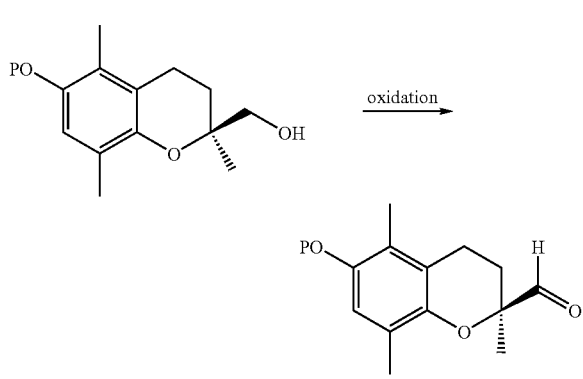

Further, various methods of forming the single-enantiomer chroman alcohol are disclosed herein.

In another aspect of this invention, it is an object of the invention to provide a method for producing the required 1-bromo (or -iodo)-2,6,10-trimethylundeca-2E,5E,9-triene. This compound is accessible through the method of this invention by treating the known acid 3,7,11-trimethyl-dodeca-2E,6E,10-trienoic acid with a combination of lead tetraacetate and iodine (or bromine in the case of the bromo compound):

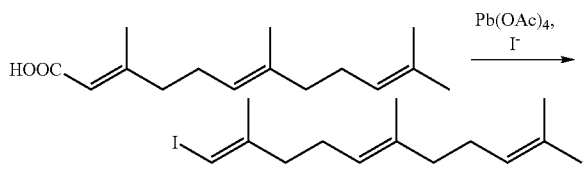

DETAILED DESCRIPTION

In accordance with the objectives stated above, the present invention, in one aspect, is a novel process for preparing d-beta-, d-gamma-, and d-delta-tocotrienol. The present process is improved over existing processes in that it is a highly convergent synthesis using more readily available starting materials. For convenience sake, the process is hereinafter described with specific reference to formation of d-beta-tocotrienol, but is equally applicable to formation of the d-gamma-, and d-delta-tocotrienol, unless stated otherwise. As used herein, a chiral compound containing greater than 90% of either the R or S enantiomer, and preferably greater than 95% of the particular enantiomer, is considered to be in the "single enantiomer" form.

The present invention provides a highly convergent process for preparing d-beta-, d-gamma-, and d-delta-tocotrienols, which are in all respects identical to those tocotrienols obtained from natural sources, through attachment of a $C_{14}$ farnesyl side chain to a suitably substituted enantiomerically pure chroman partner using coupling. The following discussion is illustrated by structures for the beta-series of compounds, but it will be understood that the isomers and homologs corresponding to the gamma- and delta-tocotrienols are also included in the invention.

In a preferred embodiment the key coupling reaction of this invention takes the form illustrated in the following chemical equation:

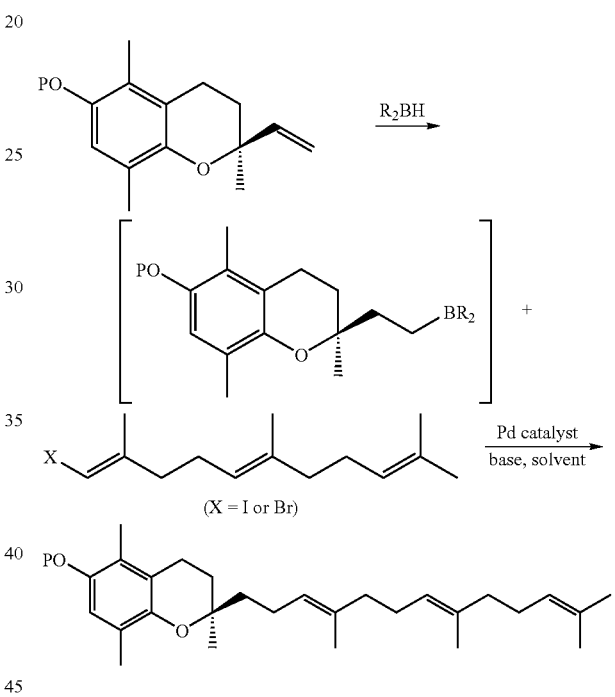

In this embodiment of the invention, the group represented by P may consist of either a hydrogen atom or a protecting group chosen from the group comprising benzyl ether, tetrahydropyranyl ether, or a trialkylsilyl ether $R_3Si$ in which the R groups are chosen from the set of $C_1$–$C_6$ straight chain or branched chain alkyl groups. In more preferred embodiments, the group P is chosen from the group containing benzyl, tert-butyldimethylsilyl, and hydrogen. In the most preferred embodiment P is hydrogen, and the halogen X is iodide.

The hydroboration reagent $R_2BH$ is chosen from that group of dialkylboranes in which the carbon-boron bond is attached to a secondary carbon center. Such dialkylboranes include dicyclohexylborane, diisopropylborane, disiamylborane, 9-borabicyclo[3.3.1]nonane ("9-BBN"), and the like. In the most preferred embodiment the borane is 9-BBN. Hydroborations of this type are discussed by N. Miyaura and A. Suzuki in *Chem. Reviews* 1995, 2457–2483.

Suitable palladium catalysts include $PdCl_2$/dppf (dichloro[1,1'-bis(diphenylphosphino)ferrocene]palladium(II) dichloromethane adduct), $Pd(PPh_3)_4$, and $Pd(P(o-tolyl_3)_4$.

Suitable bases include potassium carbonate, cesium carbonate, sodium hydroxide, potassium hydroxide, and potassium phosphate.

Suitable solvents include dimethylformamide, dimethylacetamide, water, tetrahydrofuran, 1,4-dioxane, benzene, toluene, and mixtures of these solvents.

In a preferred embodiment, the palladium catalyst is $PdCl_2(dppf)$, the solvent is dimethylformamide, and the base is potassium phosphate, at a temperature of between 20 and 100 deg C., most preferably around 50 deg C. In another preferrred embodiment, the catalyst and base are the same, but the solvent is aqueous tetrahydrofuran.

In still another preferred embodiment, the catalyst is $Pd(PPh_3)_4$, the base is aqueous NaOH or KOH or $K_3PO_4$, and the solvent is dioxane. In another preferred embodiment, the catalyst and base are the same but the solvent is a 2-phase mixture of aromatic hydrocarbon such as benzene or toluene, and water.

In a final stage, if the group P is not hydrogen, the protecting group chosen is removed by methods well known in the art and discussed by T. Greene and P. Wuts, "Protecting Groups in Organic Synthesis", Wiley, N.Y., 1999.

Preparation of (2S)-chroman diol as Precursor to 2-vinylchroman (I)

It is a further object of this invention to provide a method for preparing the requisite 2-vinylchromane intermediate in substantially enantiomerically pure form. The first route for making the 2-vinylchromane compound is from one of the corresponding enantiomerically pure (2S)-chroman diols shown specifically below as, (2S) 2-hydroxymethyl-6-hydroxy-2,5,8-trimethylchroman (beta-series), (2S) 2-hydroxymethyl-6-hydroxy-2,7,8-trimethylchroman (gamma-series), and (2S) 2-hydroxymethyl-6-hydroxy-2,8-dimethylchroman (delta-series).

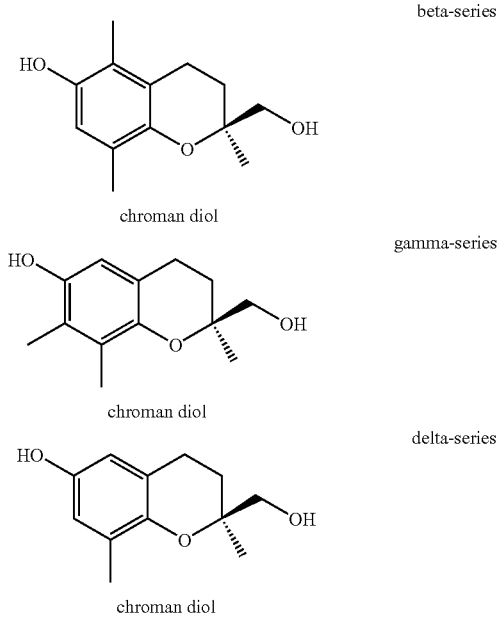

(Reference is hereinafter made to the beta-series chroman diol for convenience.) Four methods for making the enantiomerically pure (2S) chroman diol follow.

In the first method for forming the single enantiomer chroman diol, (2S) 2-hydroxymethyl-6-hydroxy-2,5,8-trimethylchroman for use as starting material in the present tocotrienol syntheses, the known compound methyl-2-methyl-4-hydroxybut-2-ene is reacted with 2,5-dimethylhydroquinone in the presence of a Lewis acid catalyst in a condensation reaction wherein the hydroxyl group is removed from the ester chain forming a cation which replaces the hydrogen atom at the C-3 ring position of the hydroquinone ring to provide an ester-substituted hydroquinone, as shown:

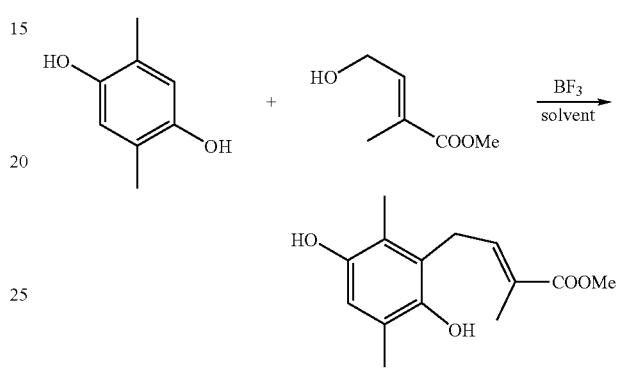

While the use of the methyl ester shown is preferred, it is understood that other esters such as the ethyl, propyl, butyl, benzyl, and the like may also be utilized. The preferred catalyst is boron trifluoride. The preferred solvent is tetrahydrofuran or a symmetrical or unsymmetrical dialkyl ether having no more than 8 carbon atoms. Other Lewis acids such as aluminum trichloride, ferric chloride, stannic chloride, and the like may be used instead of boron trifluoride. This reaction can also be conducted in a hydrocarbon solvent such as benzene, toluene, xylenes, and the like. It is also possible to carry out this reaction using a monoprotected version of the dimethylhydroquinone such as 2,5-dimethylhydroquinone monobenzoate, monotosylate, or methyl or benzyl ether.

The ester-substituted hydroquinone is then treated with a strong acid such as HCl, sulfuric acid, p-toluenesulfonic acid, methanesulfonic acid, trifluoroacetic acid, or trifluoromethanesulfonic acid in a solvent such as a dialkyl ether or tetrahydrofuran, hydrocarbon such as toluene, benzene, or an ester solvent such as methyl, ethyl, or butyl acetate to provide a racemic chroman-2-carboxylic estser. This reaction is preferably carried out at a temperature of between 0 and 100 deg C. The racemic chroman-2-carboxylic ester product of this reaction is then isolated by conventional means and subjected to reduction of the ester group to the hydroxyl oxidation state.

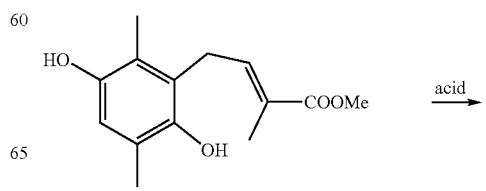

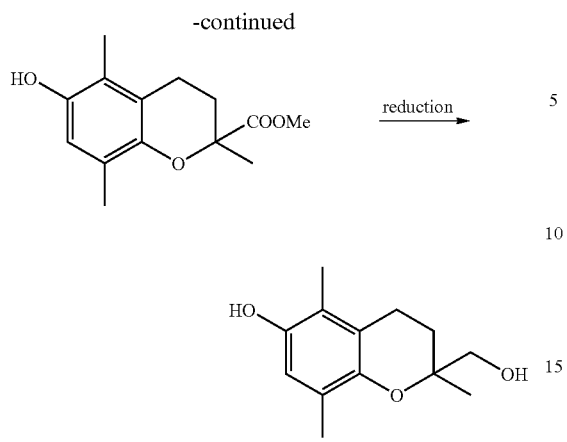

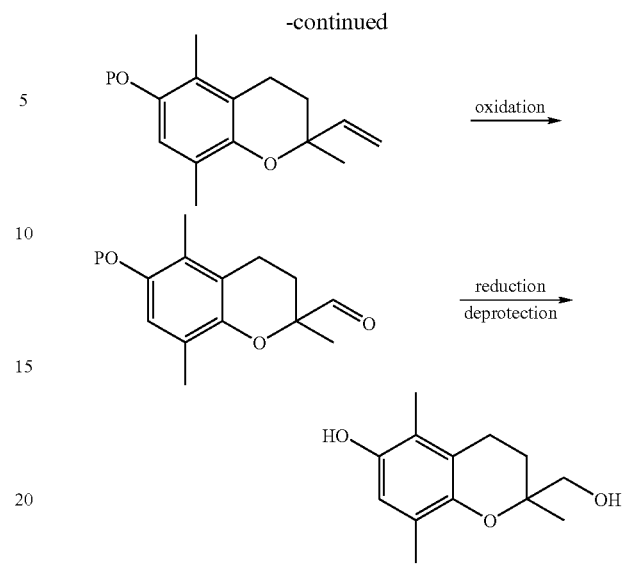

The preferred reagent for carrying out this reduction is a hydride reagent such as lithium aluminum hydride, diisobutyl aluminum hydride, or sodium bis(2-methoxyethoxy) aluminum hydride. Other preferred reagents include diborane or the technique of catalytic hydrogenation using a catalyst such as rhodium on alumina, platinum on carbon, platinum on alumina, and the like, under a pressure of between about 20 to about 2000 psi of hydrogen. It is most preferred to use sodium bis(2-methoxyethoxy)aluminum hydride in toluene, tetrahydrofuran, or dialkyl ether solvents at temperatures between about −20 and about +50 deg C.

The resulting racemic chromanol compound is then subjected to kinetic resolution by reaction with succinic anhydride in the presence of a suitable lipase enzyme catalyst such as the preferred Amano PS-30 lipase, either in the powdered form provided by the manufacturer or supported on a suitable inert support such as Celite filter-aid, using an inert solvent such as tert-butyl methyl ether at temperatures between 0 and +40 deg C. This procedure is perfectly analogous to that taught by Hyatt and Skelton (*Tetrahedron Asymmetry* 8, 523–526 (1997)), and provides, after isolation of the succinate ester of the (S) enantiomer (which is in the same configuration as the natural (R) tocotrienols) and subsequent hydrolytic removal of the succinate ester group as taught by Hyatt and Skelton, the pure single-enantiomer (2S) chromanol having the structure and absolute configuration as the compound shown by formula (V).

In the second method for forming the single enantiomer chroman diol, (2S) 2-hydroxymethyl-6-hydroxy-2,5,8-trimethylchroman for use as starting material in the present tocotrienol syntheses, a suitably monoprotected 2,5-dimethylhydroquinone is reacted with the compound 3-hydroxy-3-methyl-1,4-pentadiene to produce 2-vinyl-2,5,8-trimethylchroman-6-ol:

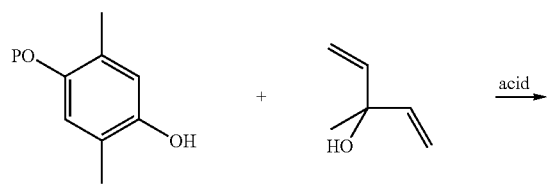

In this second embodiment, the protecting group may be chosen from those phenolic hydroxyl protection groups known and discussed by Greene and Wuts as referenced above. It is preferred that the protecting group be chosen from the group consisting of acetate, benzoate, p-toluenesulfonatae, methanesulfonate, and benzenesulfonate. It is most preferred that the protecting group is acetate or benzoate.

The acid catalyst for the condensation reaction may be a Lewis acid such as zinc chloride, boron trifluoride, or aluminum trichloride, or a Bronsted acid such as a mineral acid or trifluoroacetic acid, as taught by F. Ismail et al., *Tetrahedron Letters* 33, 3795–3796 (1992). It is preferred that the catalyst be trifluoroacetic acid, and the solvent be water. The reaction may be run between about −20 deg C. and +40 deg C.; it is preferred that it be done at about 20 deg C.

The oxidative cleavage of the vinyl group may be carried out using techniques well known in the art, such as the use of ozone, sodium dichromate, chromium trioxide, ruthenium tetrachloride and oxygen, or periodic acid/manganese dioxide. For a discussion of these reagents and typical reaction conditions, see J. March, "Advanced Organic Chemistry", 4th ed., Wiley, N.Y., 1992, pp1177–1182. In a most preferred embodiment the oxidation is accomplished by treatment with ozone, followed by zinc in acetic acid or by sodium borohydride, or by hydrogen gas at a pressure of between 15 and 50 PSI in the presence of a palladium or platinum or nickel catalyst such as 5% Pd on charcoal (preferred). In this embodiment the illustrated intermediate aldehyde is not produced, but the initially formed ozonide is reduced directly to the desired racemic chroman alcohol. The remaining protecting group my then be removed by treatment with appropriate reagents as taught by Greene and Wuts, such as sodium or potassium hydroxide, potassium carbonate, and the like, to produce an unprotected chroman alcohol which may be converted to the necessary single-enantiomer alcohol by the process technology of Hyatt and Skelton, as discussed in a previous embodiment.

In the third method for forming the single enantiomer chroman diol, (2S) 2-hydroxymethyl-6-hydroxy-2,5,8-trimethylchroman for use as starting material in the present tocotrienol syntheses 2,5-dimethylhydroquinone is suitably protected using a protecting group chosen from the group comprising benzyl ether, acetate, benzoate, p-toluenesulfonate, tetrahydropyranyl ether, and the like, and then brominated in a position ortho to the remaining phenolic hydroxyl group to form a protected bromodimethylhydroquinone. The protecting step may be conducted either before or after the bromination step. In a most preferred embodiment the protecting group is the benzyl ether, and the bromination is accomplished using N-bromosuccinimide and a catalytic amount of a $C_1$–$C_{10}$ trialkylamine, preferably a highly sterically hindered amine such as diisopropylethylamine.

Reaction of the protected bromodimethylhydroquinone with isoprene oxide is then carried out under catalysis with a suitable palladium catalyst such as $Pd(Ph_3P)_4$, $Pd_2(dba)_3$/$R_3P$ (where dba=dibenzylideneacetone, and R=phenyl, o-tolyl, or alkyl having from 1 to 8 carbon atoms), or other homogeneous $Pd^0$ catalyst. The use of such catalysts is discussed in detail by L. Hegedus, "Transition Metals in the Synthesis of Complex Organic Molecules", University Science Books, Mill Valley, Calif., 1994, Chapt. 9. In a preferred embodiment the catalyst is tetrakis(triphenylphosphine)palladium, the solvent is an ether such as diethyl ether or tetrahydrofuran, an ester such as ethyl acetate, or an inert aliphatic or aromatic hydrocarbon solvent having from 5 to 18 carbon atoms. In a most preferred embodiment the solvent is tetrahydrofuran and the temperature is about 10 to about 30 deg C.

preferably between 50 and 85 deg C. The product of this reaction is a protected chromene as shown in the above scheme.

The unwanted 3,4-olefinic linkage of the protected chromene is next reduced using catalytic hydrogenation, a well-known process in the art. The reaction is carried out in an inert solvent such as a $C_1$–$C_8$ alcohol, and ester such as methyl acetate or ethyl acetate, or an ether solvent having from 2 to 8 carbon atoms. The catalyst is chosen from the group comprising palladium on an inert support and platinum on an inert support. In a preferred embodiment the solvent is ethyl alcohol and the catalyst is 5% Pd on charcoal. Hydrogen is supplied to the reaction at a pressure of between 15 and 250 psi, preferably between 30 and 60 psi, and at a temperature about 0 deg C. and about 50 deg C. Under conditions of catalytic hydrogenation, the benzylic protecting groups are removed and the 3,4-double bonds are reduced. The resulting racemic chroman alcohol is then converted to the necessary single enantiomer chroman as described in a previous embodiment.

It should be noted that an existing fourth method of producing the racemic chroman diol is taught by Fukumoto et al in U.S. Pat. No. 5,495,026. Fukumoto et al disclose a process for producing chromans which comprises reacting a phenol, a formaldehyde and an unsaturated compound having carbon-carbon double bond in the presence of a secondary amine and an acid at a temperature between about 100° C. to about 200° C. to produce a chroman, as shown below:

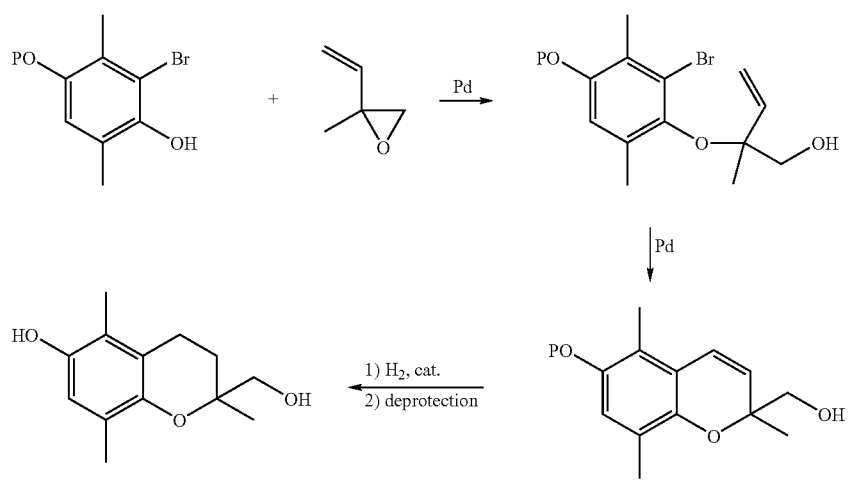

The resulting compound, with or without the addition of an additional protecting group to the primary alcohol functional group (if it is desired to use a protecting group, the most preferred group is the benzyl ether), is subjected to a palladium-catalysed cyclization reaction (Heck reaction) using as catalyst $Pd(OAc)_2$ in the presence of a $C_1$–$C_8$ phosphine such as triphenylphosphine, tri(o-tolyl)phosphine, tributylphosphine, and the like. The solvent is chosen from the group comprising dimethylformamide, dimethyl acetamide, N-methylpyrollidone, and acetonitrile. In a preferred embodiment the phosphine is triphenylphosphine and the solvent is dimethylformamide. The reaction is carried out at a temperature between 0 deg C. and 150 deg C. The preferred range is between 30 and 100 deg C. and most

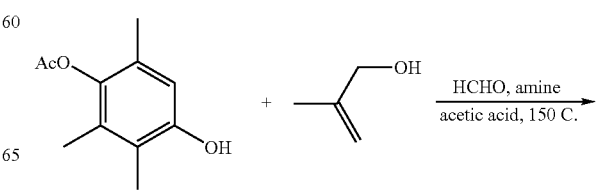

-continued

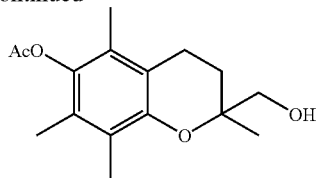

Preparation of 2-chroman aldehyde as Intermediate

Having utilized one of the four methods of this invention to produce the single-enantiomer chroman alcohol, it is a further object of this invention to show how it may be converted to the single-enantiomer vinylchroman required for exercise of the invention. To this end the alcohol may be oxidized by methods known in the art to the corresponding aldehyde:

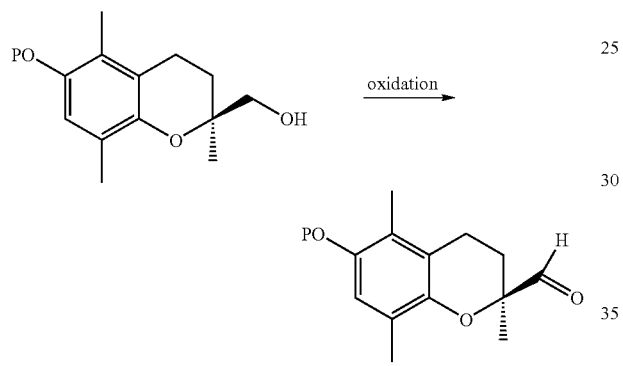

For a discussion of methods of accomplishing this type of oxidation, see M. Hudlicky, "Oxidations in Organic Chemistry", ACS, Washington, D.C. 1990, pp. 114–126. In preferred embodiments of this invention, the oxidation is carried out using a combination of dimethylsulfide and N-chlorosuccinimide or chlorine gas, or oxalyl chloride/ dimethylsulfoxide/triethylamine at temperatures from −60 deg C. to 0 deg C., or oxygen or air and a transition metal catalyst chosen from the group Pt on carbon, $PtO_2$, Cu, or Ag either in a solvent such as an inert aliphatic hydrocarbon having between 6 and 18 carbon atoms, or in the gas phase. In a most preferred embodiment the oxidation is carried out using oxalyl chloride/dimethylsulfoxide/triethylamine. Such an oxidation in a very similar molecule is taught by Hyatt and Skelton, *Tetrahedron Asymmetry* 8, 523–526 (1997).

Preparation of 2-vinylchroman from 2-chroman aldehyde

It is a further purpose of this invention to provide a method for conversion of the above-prepared single enantiomer aldehyde to the vinylchroman molecule (I) required for the crucial carbon-carbon bond-forming step of the invention. To this end, methods known in the art as Wittig and Wittig-Homer reactions may be employed; such reactions are discussed by J. March, "Advanced Organic Chemistry", Wiley, N.Y. 1992, pp. 956–963.

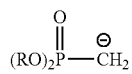

In one embodiment of this invention, the phosphonium ylid reagent has R=phenyl. In another modification of this invention, the alkenylating reagent is a phosphonate reagent of the type usually referred to as a Homer-Emmons or Wittig-Homer reagent, and has the structure $$(RO)_2\overset{O}{\overset{\|}{P}}-\overset{\ominus}{CH_2}$$

wherein the group R is chosen from the set of $C_1$–$C_6$ straight or branched-chain alkyl groups. In a preferred embodiment of the invention, the phosphonate Wittig-Horner reagent wherein R=methyl or ethyl is used.

Alternative Methods for Forming (2S)-vinylchromane

Knierzinger et al, U.S. Pat. No. 5,110,955, disclose alternative methods for forming vinyl chromane for tocopherol synthesis by means of a rhodium- or palladium-diphosphine complex. An improvement on the method of Knierzinger et al is disclosed by Trost, et al in *Synthesis of Chiral Chromans by the Pd-Catalyzed Asymmetric Allylic Alkylation (AAA): Scope, Mechanisms, and Applications, J. Am. Chem. Soc.* 2004, 126, 11966–11983.

Preparation of C14 Sidechain Compound

It is a further object of this invention to provide a method for preparing the 14-carbon halo compound necessary for implementation of the invention. In this aspect of the invention, the known acid 3,7,11-trimethyl-2E,6E,10-trienoic acid is prepared by methods known in the art from the well-known terpene alcohol farnesol. This acid is then subjected to treatment with a mixture of lead tetraacetate and iodine (or bromine), whereupon decarboxylative halogenation takes place to provide the desired compound, 1-iodo-(or bromo-)2,6,10-trimethylundeca-1E,5E,9-triene.

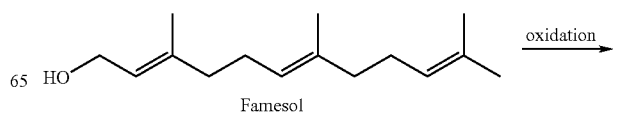

-continued

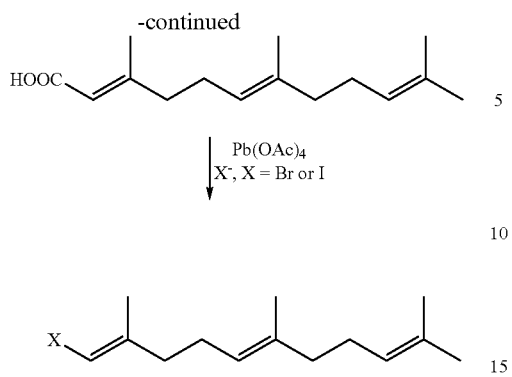

In this preferred embodiment, the final decarboxylative halogenation uses X=I and is an example of the Hunsdiecker reaction, discussed in detail by J. March, "Advanced Organic Chemistry", Wiley, N.Y. 1992, pp. 730–732. In other embodiments, this conversion may be carried out using a silver salt and halogen instead of the preferred lead reagent discussed above.

This invention is further illustrated by the following example of a preferred embodiment thereof. This example is included merely for purposes of illustration and is not intended to limit the scope of the invention.

EXAMPLE

Preparation of d-beta-tocotrienol

A 50-ml, 3-necked flask is equipped with magnetic stirrer, septum, reflux condenser, and argon atmosphere. The flask was charged with 1.20 grams (5.5 mmol) of (S)-2-vinyl-2,5,8-trimethychromanol and 2.5 ml of anhydrous tetrahydrofuran. There was added at 0 deg C. 14 ml of a 0.4 molar solution of 9-BBN in tetrahydrofuran. The solution was allowed to warm to 20 deg C. and stirred for 4 hrs. There was then added 0.11 gram (0.15 mmol) of dichloro[1,1'-bis(diphenylphosphino)ferrocene]palladium(II)dichloride dichloromethane adduct followed by a solution of 1.6 grams (5.0 mmol) of 1-iodo-2,6,10-trimethyl-1E,5E,9-undecatriene in 12.5 ml of tetrahydrofuran. This was followed by addition of 5 ml of an aqueous 3M NaOH solution. The resulting mixture was stirred under reflux for 12 hours, cooled to rt, and treated with 2 ml of 30% hydrogen peroxide. The mixture was diluted with 20 ml of hexane, stirred, and the organic phase separated, washed with brine, dried over anhydrous magnesium sulfate, and stripped of solvent under reduced pressure to afford d-beta-tocotrienol in about 85% of the theoretical yield.

The invention has been described in detail with particular reference to preferred embodiments thereof, but it will be understood that variations and modifications can be effected within the spirit and scope of the invention.

The invention claimed is:

1. A process of forming a d-tocotrienol comprising:
   a) providing a (2S)-vinylchroman compound having the formula shown by (I), in single enantiomer form;

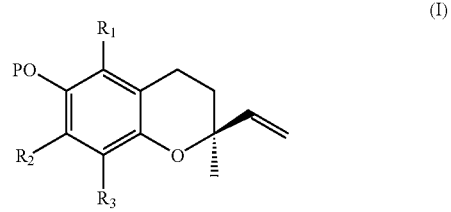

b) converting said (2S)-vinylchroman compound of (I) to an organoborane having the formula shown by (II) by way of a hydroboration reaction; and

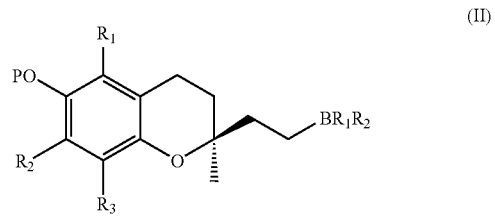

c) providing 1-bromo-2,6,10-trimethylundeca-1E,5E,9-triene or 1-iodo-2,6,10-trimethylundeca-1E,5E,9-triene;

d) coupling said organoborane of (H) with 1-bromo-2,6,10-trimethylundeca-1E,5E,9-triene or 1-iodo-2,6,10-trimethylundeca-1E,5E,9-triene, under conditions of palladium-catalyzed cross-coupling to form a d-tocotrienol product of formula (III),

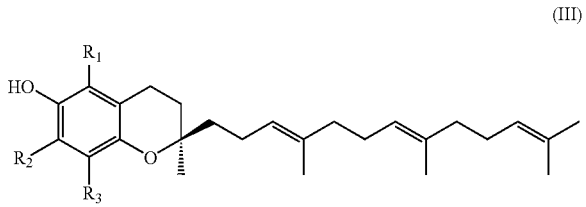

wherein $R_1$ is a hydrogen atom or methyl group, $R_2$ is a hydrogen atom or methyl group, and $R_3$ is a methyl group, except that $R_1$ and $R_2$ are not both methyl groups, further wherein P is a hydrogen atom or a protecting group.

2. The process according to claim 1 wherein P is hydrogen or a protecting group selected from the group consisting of p-toluenesulfonate ester, benzenesulfonate ester, methanesulfonate ester, benzyl ether, methyl ether, 2-tetrahydropyranyl ether, and 2-tetrahydrofuranyl ether, benzyl ether, tetrahydropyranyl ether, and a trialkylsilyl ether $R_3Si$ wherein the alkyl groups are chosen from the set of $C_1$–$C_6$ straight chain or branched chain alkyl groups.

3. The process according to claim 1 wherein said P is hydrogen and said organoborane is coupled with 1-iodo-2,6,10-trimethylundeca-1E,5E,9-triene.

4. The process according to claim 1 wherein said d-tocotrienol product produced is in greater than 90.0 percent of the (R) enantiomeric form.

5. The process according to claim 1 wherein said d-tocotrienol product formed is d-beta-tocotrienol, wherein each of $R_1$ and $R_3$ is a methyl group and $R_2$ is a hydrogen atom.

6. The process according to claim 1 wherein said d-tocotrienol product formed is d-gamma-tocotrienol, wherein $R_1$ is a hydrogen atom and each of $R_2$ and $R_3$ is a methyl group.

7. The process according to claim 1 wherein said d-tocotrienol product formed is d-delta-tocotrienol, wherein each of $R_1$ and $R_2$ is a hydrogen atom and $R_3$ is a methyl group.

8. The process according to claim 1 wherein said hydroboration reaction is conducted using a dialkylborane reagent selected from the group consisting of dicyclohexylborane, diisopropylborane, disiamylborane, and 9-borabicyclo[3.3.1]nonane.

9. The process according to claim 1 wherein said step of providing said (2S)-vinylchroman compound of (I), in single enantiomer form is conducted by a method comprising the steps of
a) providing a 2-chroman aldehyde compound having the formula shown by (IV), in single enantiomer form; and

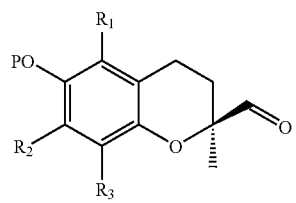

(IV)

b) converting said 2-chroman aldehyde to said (2S)-vinylchroman compound of (I) by way of a Wittig olefination reaction, wherein $R_1$ is a hydrogen atom or methyl group, $R_2$ is a hydrogen atom or methyl group, and $R_3$ is a methyl group, and further wherein P is hydrogen or a protecting group selected from the group consisting of p-toluenesulfonate ester, benzenesulfonate ester, methanesulfonate ester, benzyl ether, methyl ether, 2-tetrahydropyranyl ether, and 2-tetrahydrofuranyl ether, benzyl ether, tetrahydropyranyl ether, and a trialkylsilyl ether $R_3Si$ wherein the alkyl groups are chosen from the set of $C_1$–$C_6$ straight chain or branched chain alkyl groups.

10. The process according to claim 9 wherein said step of providing a 2-chroman aldehyde compound having the formula shown by (IV) is conducted by a method comprising the steps of
a) providing a (2S) 2-hydroxymethyl-6-hydroxy-alklychroman compound having the formula shown by (V), in single enantiomer form; and

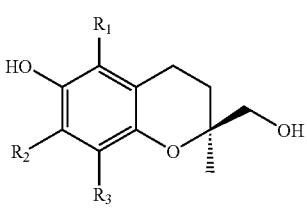

(V)

b) oxidizing said (2S)-chroman alcohol of (V) to provide the single enantiomer (2S)-chroman aldehyde of formula (IV), wherein $R_1$ is a hydrogen atom or methyl group, $R_2$ is a hydrogen atom or methyl group, and $R_3$ is a methyl group.

11. The process according to claim 10 wherein said step of providing a (2S) 2-hydroxymethyl-6-hydroxy-alklychroman compound having the structure shown by (V), in single enantiomer form is conducted by a method comprising the steps of
a) providing methyl-2-methyl-4-hydroxy-2-butenoate;
b) reacting said methyl-2-methyl-4-hydroxy-2-butenoate with 2,5-dimethylhydroquinone under the influence of Lewis acid catalysis to provide the substituted hydroquinone having the structure of formula (VI);

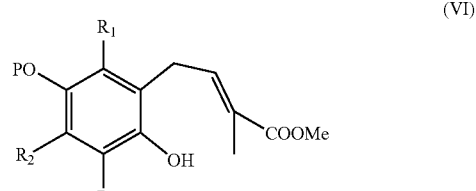

(VI)

c) cyclizing said substituted hydroquinone of (VI) under the influence of a protic or Bronsted acid to provide a racemic chroman ester having the structure of formula (VII);

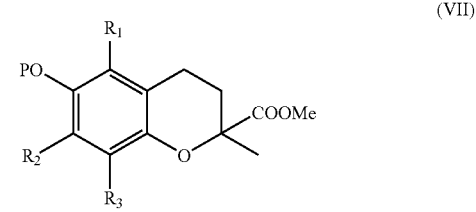

(VII)

d) reducing said racemic chroman ester of (VII) to its corresponding racemic chroman alcohol; and
e) resolving said racemic chroman alcohol to form said (2S) 2-hydroxymethyl-6-hydroxy-alklychroman compound, wherein $R_1$ is a hydrogen atom or methyl group, $R_2$ is a hydrogen atom or methyl group, and $R_3$ is a methyl group, and further wherein P is hydrogen or a protecting group selected from the group consisting of p-toluenesulfonate ester, benzenesulfonate ester, methanesulfonate ester, benzyl ether, methyl ether, 2-tetrahydropyranyl ether, and 2-tetrahydrofuranyl ether, benzyl ether, tetrahydropyranyl ether, and a trialkylsilyl ether $R_3Si$ wherein the alkyl groups are chosen from the set of $C_1$–$C_6$ straight chain or branched chain alkyl groups.

12. The process according to claim 10 wherein said step of providing a (2S) 2-hydroxymethyl-6-hydroxy-alklychroman compound having the structure shown by (V), in single enantiomer form is conducted by a method comprising the steps of
a) reacting a protected 2,5-dimethylhydroquinone with 3-methyl-3-hydroxy-1,4-pentadiene under the influence of a Bronsted acid to form a racemic 2-vinyl-2,5,8-trimethylchroman-6-ol having the structure of formula (VIII);

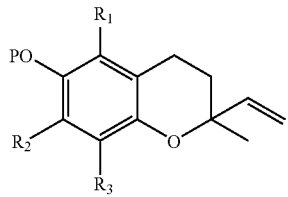

(VIII)

b) oxidatively cleaving said vinylchroman compound of (VIII) to form a chroman-2-aldehyde having the structure of formula (IX);

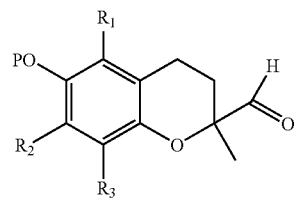

(IX)

c) reducing said chroman-2-aldehyde of (IX) to its corresponding racemic chroman-2-alcohol; and (d) resolving said racemic chroman-2-alcohol to form said (2S) 2-hydroxymethyl-6-hydroxy-alklychroman compound of formula (V), wherein $R_1$ is a hydrogen atom or methyl group, $R_2$ is a hydrogen atom or methyl group, and $R_3$ is a methyl group, and further wherein P is hydrogen or a protecting group selected from the group consisting of p-toluenesulfonate ester, benzenesulfonate ester, methanesulfonate ester, benzyl ether, methyl ether, 2-tetrahydropyranyl ether, and 2-tetrahydrofuranyl ether, benzyl ether, tetrahydropyranyl ether, and a trialkylsilyl ether $R_3Si$ wherein the alkyl groups are chosen from the set of $C_1-C_6$ straight chain or branched chain alkyl groups.

13. The process according to claim 10 wherein said step of providing a (2S) 2-hydroxymethyl-6-hydroxy-alklychroman compound of formula (V), in single enantiomer form is conducted by a method comprising the steps of a) reacting a protected 2,5-dimethyl-3-bromohydroquinone molecule with isoprene oxide (1-methyl-1-vinyloxirane) under the influence of a palladium catalyst to provide an allylic ether compound having the structure of formula (X);

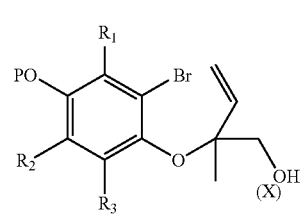

(X)

b) adding a protecting group to the primary hydroxyl group of said allylic ether compound of formula (X) to form a protected allylic ether compound having the structure of (XI);

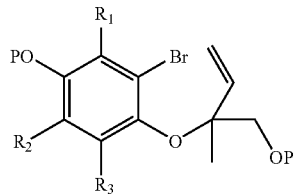

(XI)

c) cyclizing said protected allylic ether compound of (XI) using a Heck reaction to form a 3-chromene derivative having the structure of (XII);

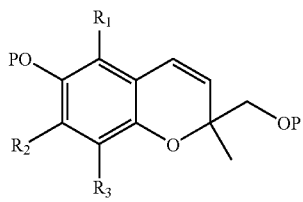

(XII)

d) hydrogenating said 3-chromene derivative of (XII) by way of catalytic hydrogenation to form a diprotected racemic 2,5,8-trimethylchroman-2-methanol;

e) removing the protecting groups from said diprotected racemic 2,5,8-trimethylchroman-2-methanol to provide a racemic 2,5,8-trimethyl-6-hydroxychroman-2-methanol; and f) resolving said racemic 2,5,8-trimethyl-6-hydroxychroman-2-methanol to form said (2S) 2-hydroxymethyl-6-hydroxy-alklychroman compound of formula (V), wherein $R_1$ is a hydrogen atom or methyl group, $R_2$ is a hydrogen atom or methyl group, and $R_3$ is a methyl group, and further wherein P is hydrogen or a protecting group selected from the group consisting of p-toluenesulfonate ester, benzenesulfonate ester, methanesulfonate ester, benzyl ether, methyl ether, 2-tetrahydropyranyl ether, and 2-tetrahydrofuranyl ether, benzyl ether, tetrahydropyranyl ether, and a trialkylsilyl ether $R_3Si$ wherein the alkyl groups are chosen from the set of $C_1-C_6$ straight chain or branched chain alkyl groups.

14. The process according to claim 1 wherein said step of providing 1-iodo-2,6,10-trimethylundeca-1E,5E,9-triene is conducted by treating 3,7,11-trimethyldodeca-2E,6E,10-trienoic acid with a lead tetraacetate and iodine.

15. The process according to claim 1 wherein said step of providing 1-bromo-2,6,10-trimethylundeca-1E,5E,9-triene is conducted by treating 3,7,11-trimethyldodeca-2E,6E,10-trienoic acid with a lead tetraacetate and bromine.

* * * * *